(12) United States Patent
Chien (10) Patent No.: US 8,998,462 B2
(45) Date of Patent: Apr. 7, 2015

(54) MULTIPLE SURFACE LED LIGHT

(76) Inventor: Tseng-Lu Chien, Walnut, CA (US)

( * ) Notice: Subject to any disclaimer, the term of this patent is extended or adjusted under 35 U.S.C. 154(b) by 467 days.

(21) Appl. No.: 12/950,017

(22) Filed: Nov. 19, 2010

(65) Prior Publication Data

US 2012/0127708 A1 May 24, 2012

(51) Int. Cl.
| F21V 14/00 | (2006.01) |
| F21S 8/08 | (2006.01) |
| F21V 17/02 | (2006.01) |
| F21V 19/00 | (2006.01) |
| F21V 19/02 | (2006.01) |
| F21V 23/06 | (2006.01) |
| F21Y 101/02 | (2006.01) |

(52) U.S. Cl.
CPC .............. *F21V 17/02* (2013.01); *F21V 19/0015* (2013.01); *F21V 19/02* (2013.01); *F21V 23/06* (2013.01); *F21Y 2101/02* (2013.01)

(58) Field of Classification Search
USPC .............. 362/640, 253, 85, 234, 421, 249.02, 362/427
See application file for complete search history.

(56) References Cited

U.S. PATENT DOCUMENTS

| 4,419,721 | A | * | 12/1983 | Gregoire et al. | ............... 362/368 |
| 6,165,010 | A | * | 12/2000 | Prazoff | ........................ 439/534 |
| 7,040,783 | B1 | * | 5/2006 | Christianson | ................. 362/396 |
| 7,210,816 | B2 | * | 5/2007 | Lin | ............................... 362/234 |
| 7,618,150 | B2 | * | 11/2009 | Chien | ............................ 362/35 |
| 8,109,643 | B2 | * | 2/2012 | Wu | ................................. 362/96 |
| 8,408,736 | B2 | * | 4/2013 | Chien | ........................... 362/235 |
| 8,408,760 | B2 | * | 4/2013 | Bornhorst et al. | ............ 362/419 |
| 8,585,260 | B2 | * | 11/2013 | Hajee et al. | .................... 362/427 |
| 8,622,563 | B2 | * | 1/2014 | Manners | ........................ 362/85 |
| 2006/0164823 | A1 | * | 7/2006 | Jao | ................................. 362/101 |
| 2011/0279064 | A1 | * | 11/2011 | Brooks et al. | ................. 315/362 |

* cited by examiner

Primary Examiner — Peggy Neils
(74) *Attorney, Agent, or Firm* — Bacon & Thomas, PLLC (57) ABSTRACT

A multiple surface LED light has at least a first surface on which LED elements are arranged to provide an illumination function and at least one other surface arranged to provide other desired functions, performances, and/or features. The said LED light has a frame or housing, and an opening that allows the exposed one of the first and other r surfaces to be changed when external force is applied to the LED light.

5 Claims, 7 Drawing Sheets

Top View  Fig 4

Side View  Fig 5

Fig 6A

Rotate LED light from 1st surface to next surface or more next surfaces.

Fig 6B

Folded two arms

Folded two arms

MULTIPLE SURFACE LED LIGHT

BACKGROUND OF THE INVENTION

This application has subject matter in common with the inventor's prior U.S. patent application Ser. Nos. 12-624,621, 12-622,100, 12-318,471, 12-318,470, 12-318,473, 12-292, 153, 12-232,505, 12-232,035, 12-149,963, 12-149,964, 12-073,095, 12-073,889, 12-007,076, 12-003,691, 12-003, 809, 11-806,711, 11-806,285, 11-806,284, 11-566,322, 11-527,628, 11,527,629, 11-498,874, 12-545,992, 12-806, 711, 12-806,285, 12-806,284, 12-566,322, 12-527,628, 12-527,629, 12-527,631, 12-502,661, 11-498,881, 11-255, 981, 11-184,771, 11-152,063, 11-094,215, 11-092,742, 11-092,741, 11-094,156. 11-094,155. 10-954,189, 10-902, 123, 10-883,719, 10-883,747, 10-341,519, 12-545,992, 12-292,580, 12-710,918, 12-622-000, 12-710,561, 12-710, 12-711,456, and 12-771,003.

The above-listed prior applications of the inventor apply optics theory to LED lights for outdoor or indoor applications and powered by alternating current (AC) or direct current (DC) supplied by and electric cord and plug for an outlet, or by a battery, transformer, solar cell, or other power source to create a plurality of LED light beams to illuminate both close areas and remote areas, the latter by projection means. Other features disclosed in the listed prior patent applications of the inventor and which may be incorporated with present invention in any combination, include the use in an LED light of more than one light source, more than one function, more than one optics means, more than one projection means, and super power saving circuits and cost saving concepts.

The market-available LED light has only one surface on which to install the LED elements that offer the light function, as well as other circuitry and components of the LED light. The current invention is an LED light with multiple surfaces, at least one of the multiple surface(s) being installed with at least one LED element that provides at least one pre-determined function, light output, color, effects, and light performance of the type that may also be provided by conventional market-available LED light devices, the other surfaces being installed with other electric devices, circuits, or components, which may be selected from receiving-units for any kind of electric device, such as outlets, sockets, adaptors, hubs, USB sockets, memory storage sockets, memory stick sockets, memory card sockets, Internet sockets, interface card sockets, prong sockets, quick connector sockets, male or female connector ends, and any electric device's connector, power connector, electric signal connector, cable connector, other light source, second light device, sound device, sensor device, alarm device, time related device or any other electric or mechanical device.

The multiple surface LED light of the current invention not only offers illumination but also offers other electric or mechanical device functions on the other surface(s) to save people money and save space by providing multiple functions for certain locations.

The multiple surface light of the current invention has a frame with an opening to enable the multiple surface LED light to change surfaces by an external force applied to the LED light. The frame and opening, depending on the number of surfaces needed, can be any design. For example, for 2 surfaces, the LED light can have a round opening and frame that allows two extended bars of the LED light to be rotated from the first surface to other surface. The LED light also can have more than two surfaces, such as three surfaces, four surfaces, five surfaces, six surfaces or N (any number of) surfaces, the opening and frame being easily designed to accommodate the number of surfaces needed.

The multiple surface LED light of the current invention may consist of desired parts and accessories selected from a frame, opening, locking means, extend bars, holding means, support means, fixing means, elastic means, screw means, clip tight means to enable the LED light to be installed on any surface by itself or in a group of LED lights, the surfaces including a main substrate of a desk, wall, ceiling, bar, tube, fence, closet, cabinet, power strip, light fixture, light bar, door, window, and rack for indoor or outdoor application, with optional waterproofing or protection from the environment.

The LEDs included on the first surface of the multiple surface LED light of the current invention may include any LED type, LED color, LED brightness, LED output, number of LEDs, shape of LED, LED dimensions, raised LEDs, flat type LEDs, SMT LEDs, recessed LEDs, and any corresponding shades, covers, lenses, or decorative parts that may be added to increase the value of the LED light. For example, when the LED light device of the current invention is arranged for desk top use, one can put any kind of home-available water bottle, milk bottle, glass, cup, balloon, light transmitting material, transparent material, or translucent material on top of the said LED elements on the first surface to provide different light effects. one does not even need a shade, cover, or lens for the LED elements because the current invention allows people to play with any kind from home-available items to change light effects.

The multiple surface LED light of the current invention can have its own frame arranged to fit on any surface by itself, including walls, ceilings, boards, cabinets, closets, and doors for indoor or outdoor use, or on any surface of a main object such as a light fixture, light set, light device, power strip, or other objects that form a finish product.

The external force that causes the multiple surface LED light device of the current invention to change to another surface may come from people, or machine or mechanical device.

The multiple surface LED light of the current invention may incorporate an electric parts and accessories selected from any combination of resistor, capacitor, IC chip, transistor, diode, sensor means, switch means, timer means, time delay means, adjustable means, sensitivity means, variable electric value means, wireless control means, transmitter and receiver means, PIR means, infrared means, Bluetooth means, photo sensors, manual switches, automatic means to make the said LED element(s) to turn on an turn off to achieve pre-determined functions, effects( ) and performance(s). The electric signal connection used by the LED light device of the current invention may incorporate conventional signal connections or apply the signal connections taught in the inventor's prior U.S. Pat. No. 7,824,185 or the inventor's copending US 2008/0266 856.

BRIEF DESCRIPTION OF THE DRAWINGS

FIGS. 1 and 1A-1D shows a first preferred embodiment of a multiple surface LED light installed in a recess and having a first surface that includes at least one LED elements. When an external force is applied to the LED light, the first surface will rotate to expose a second surface that may be fixed in position by lock means and that offers people outlets for a power source, Internet socket, and phone socket to conveniently provide multiple functions in one location on the said LED light and thereby save a lot of space, especially for a working table or under cabinet light fixture.

DETAILED DESCRIPTION OF THE PREFERRED EMBODIMENTS

Figure 1:
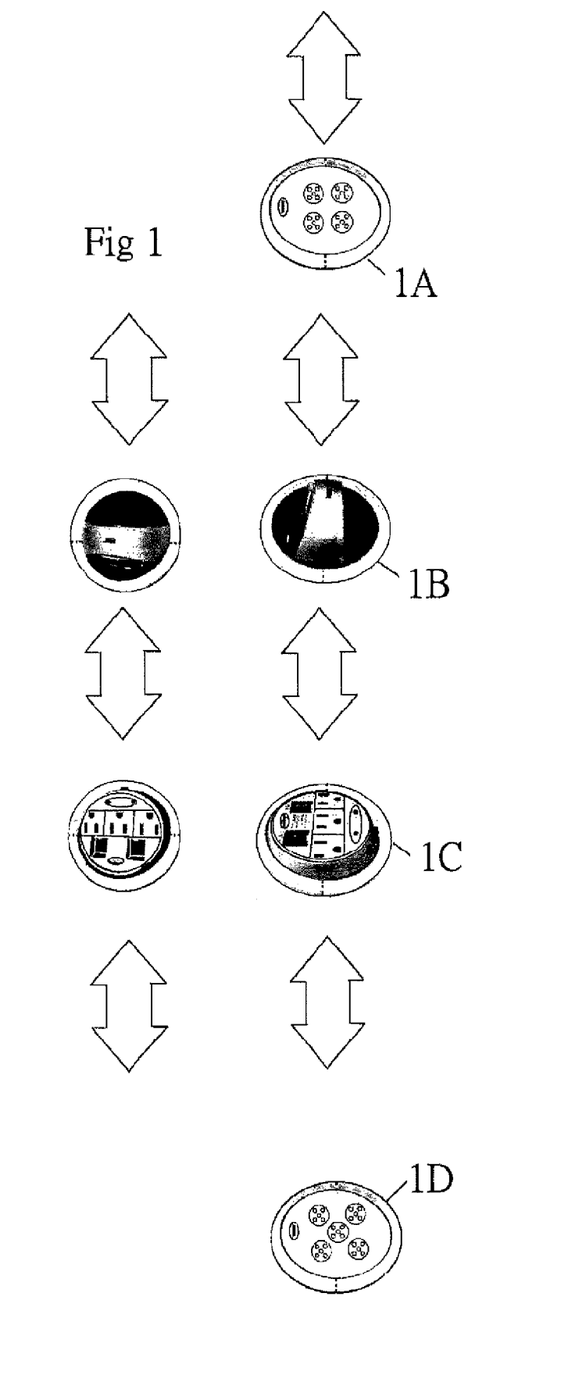

FIG. 1 a first preferred embodiment of a multiple surface LED light installed in a recess and having a first surface shown in FIG. 1A that includes at least one LED element. When an external force is applied to the LED light to cause it to rotate, as indicated by FIG. 1B, a second surface is exposed, as shown in FIG. 1C, and fixed in position by lock means to offer people outlets for a power source, an Internet socket, and a phone socket, thereby providing people with additional convenient functions at the same location as the LED light. The multiple surface LED light can continue to rotate to return to the first surface, as indicated by FIG. 1D when an external force is again applied to the LED light so that it can be continuously rotated As indicated in the notes included in FIGS. 1A-1D, the LED light may have more than two surfaces and rotate to each of the surfaces successively, with the LED light being provided with poles to enable rotation. The second surface illustrated in FIG. 1C may not only include power outlets and internet/phone connections, the second surface may include USB ports, digital data storage device ports, memory device ports, charger sockets, jacks, adaptors, and various plug means and other connectors. The shape of the surface is not limited to circular, but may also include other frame shapes such as hexagonal or multiple edge shapes, and the number of surfaces may for example be six, four, or three as well as the illustrated two sides.

The single location of the multiple surfaces therefore can provide multiple electric applications, as shown in FIG. 1, which will save a lot of space, especially for a working table or under cabinet light fixture.

Figure 2A:
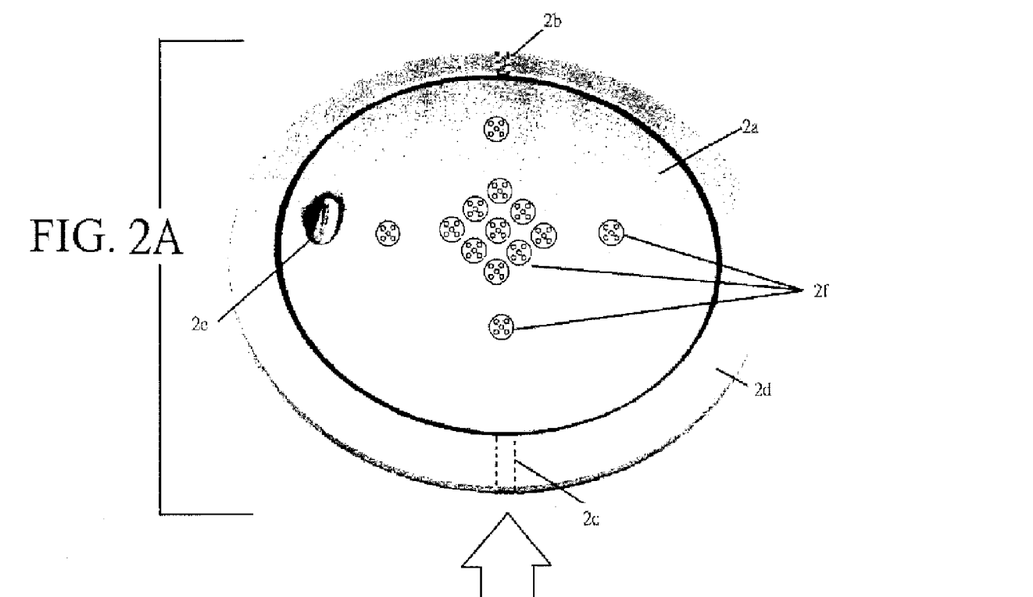
FIGS. 2A, 2B, 3A, and 3B illustrate one application for the first preferred embodiment in which the multiple surface LED light been applied to a ceiling, walls, door, or other surface by itself without any other main objects, substrates, or housing means, i.e., in which the multiple surface LED light is directly installed in or built-into a building, house, large furniture, or other permanent fixture such as ceiling, wall, door, closet, or cabinet, rather than having a separate housing as is the case with power strips, LED light fixtures, light devices, and light bars.
Figure 2B:
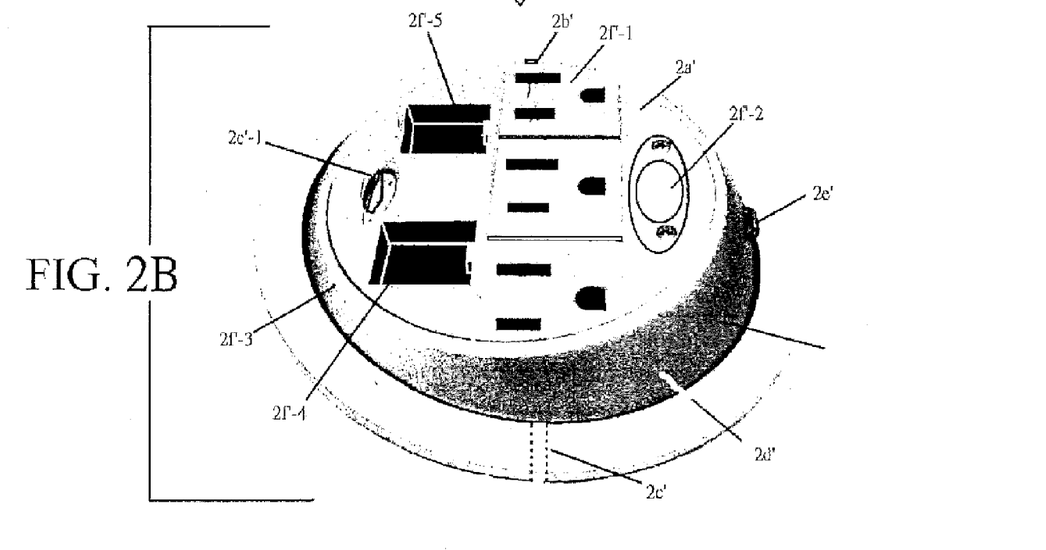
Figure 3A:
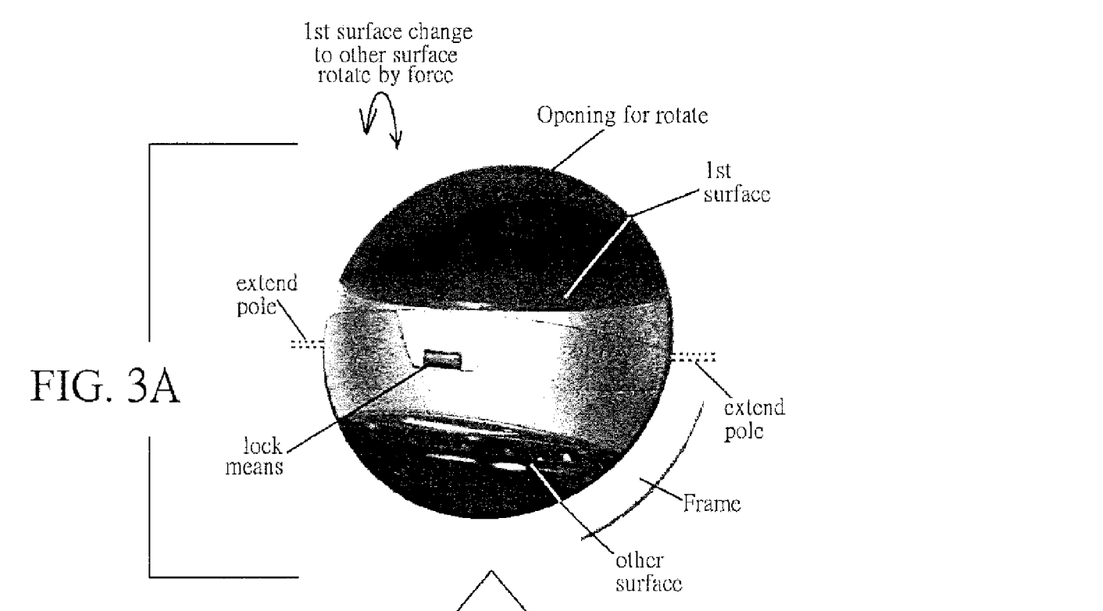
Figure 3B:
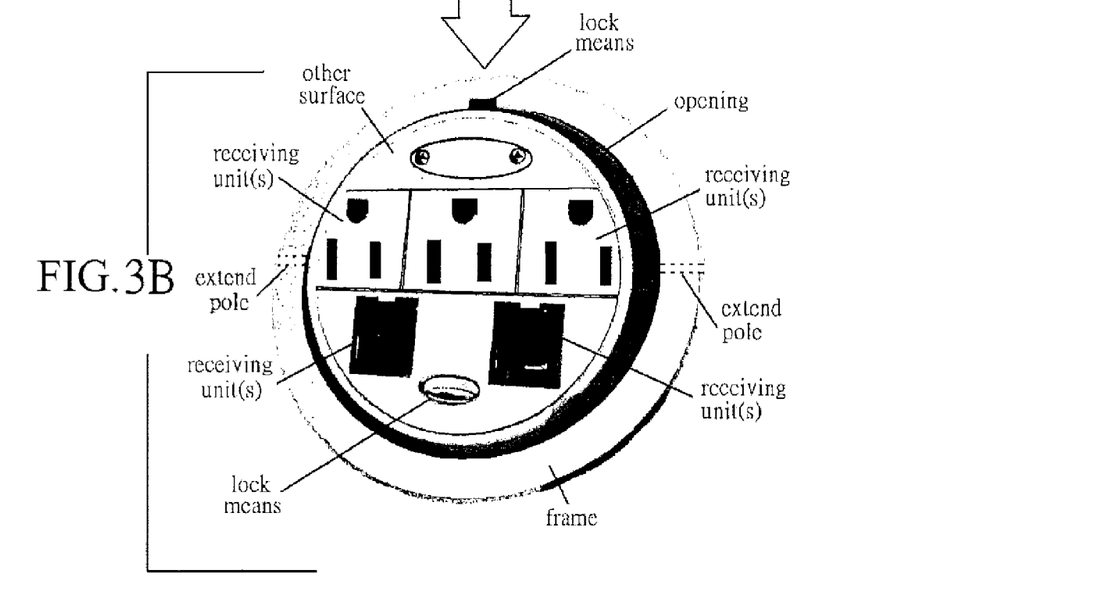
Figure 4:
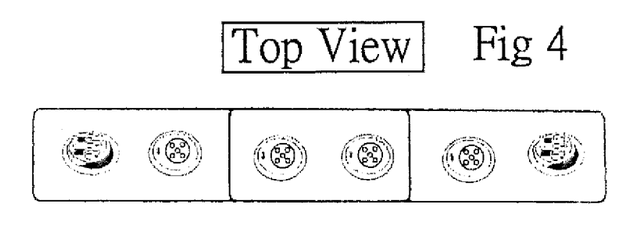
FIGS. 4, 5, 6A, 6B, 7, 8, 9, 10, 10A, 10B, 10C, and 11 illustrate other applications of the multiple surface LED light of the first preferred embodiment in which the multiple surface LED light been applied to other main objects, other substrates, or other housing means in the form of individual existing products available in the marketplace, such as power strips, light fixtures, extension cords (such as the ones disclosed in the inventor's U.S. Pat. No. 7,824,185), wall outlet devices, LED light devices (such as the one disclosed in the inventor's U.S. Pat. No. 7,618,150), foldable devices, extendable devices (such as the one described in the inventor's U.S. Pat. No. 7,722,230, removable devices (such as the one described in the inventor's U.S. Pat. No. 7,726,839), and transforming devices (as described in the inventor's U.S. Pat. No. 7,726,841). The current invention modifies these existing products to become even more useful and practical items because it provides more functions in the same space occupied by the original products.
Figure 5:
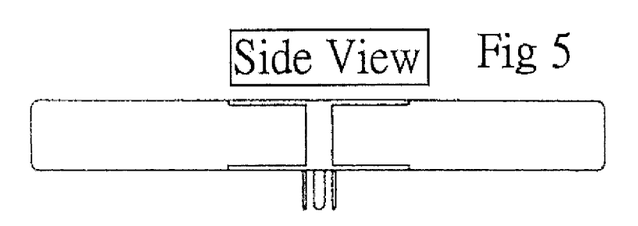
Figure 6A:
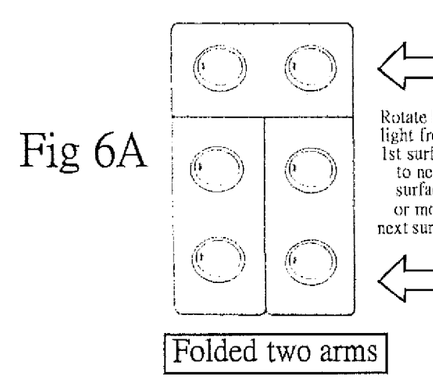
Figure 6B:
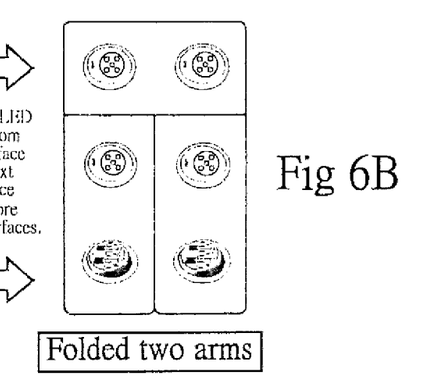
Figure 7:
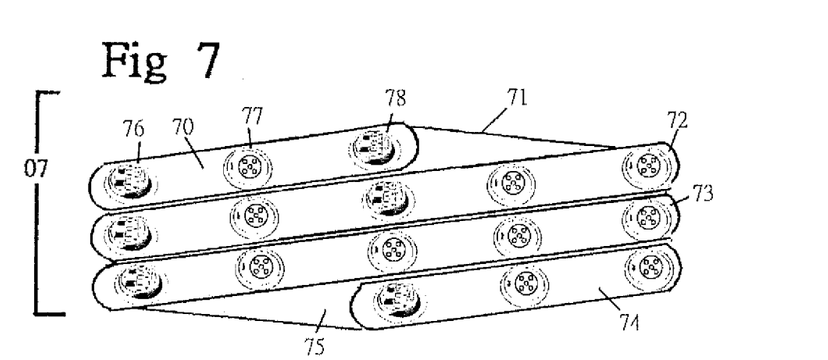
Figure 8:
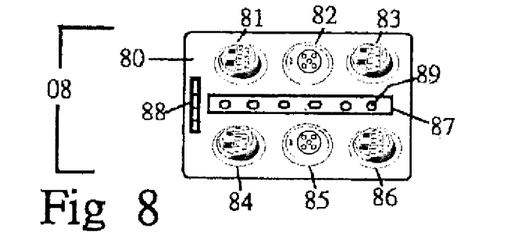
Figure 9:
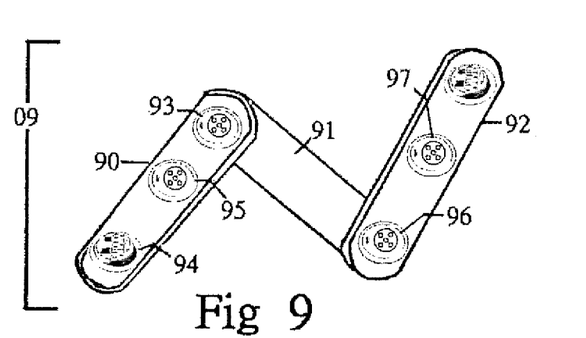

FIGS. 2 and 3 an application of the light device of the first preferred embodiment, in which the multiple surface LED light may be applied to a ceiling, walls, door, or even a surface by itself without any other main object, substrate, or housing. The phrase "by itself" means that the multiple surface LED light is directly installed in a building, house, furniture, ceiling, wall, door, closet, or cabinet rather than being provided as a discrete unit as is the case with conventional power strips, LED light fixtures, light devices, and light bars.

As shown in FIG. 2, the first surface (2a) has a plurality LEDs or an LED dot matrix array made up of LED sets (2f) installed on the first surface (2a), and two bars including an extended top bar (2b) and low bar (2c) that provide a pivot axis about which the LED light can be rotated. The two extended bars also have an inner channel to enable electric signal delivery from ends of the bars into the LED light. The electric connections of the embodiment of FIG. 2 may correspond to inventor's prior electric connections shown in the drawing figures on pages 8 to 13 of the present drawings, or may utilize any other conventional electric signal delivery means. A lock means (2e) enables the LED light to be locked in a particular position without changing the surface to another surface. For example, when the LED light is in the position shown in FIG. 2B, if a lock means were not provided it would be too easy to rotate the device to a different position, which could be very dangerous in the case where a prong means has been inserted into the outlet socket(s) (2f-1). The lock means (2e) (2e') (2e'-1) not only provides a locking functions, but also may act as s release means to enable the LED light to be changed from a first surface to other surfaces as needed. The other surfaces (2a') may has the outlet sockets (2f'-1), Internet sockets (2f'-5), phone sockets (2f'-4), and/or sensor means (2f'-2) to offer people a very convenient LED light with multiple functions when the surfaces are changed.

FIG. 3 shows additional details of the construction of the LED light of FIG. 2 of LED light and the manner in which it rotates from the first surface, shown in FIG. 3A, to another surface shown in FIG. 3B, by rotating about the extended poles upon release of the lock means shown therein. The respective surfaces shown in FIGS. 3A and 3B correspond to those shown in FIGS. 2A and 2B.

FIGS. 4, 5, 6A, 6B, 7, 8, and 9 show the manner in which preferred multiple surface LED lights are applied directly to a ceiling, walls, or the surface of a building or house, and also to existing electric products. Any of the existing products that do not include the light device of the present invention will become out-of-date. More specifically, FIGS. 4, 5, 6A, 6B, 7, 8, 9 all show LED light bars, or outlet devices, extension cords, or power strips which have been modified to include the multiple surface light devices of the present invention and to be foldable as disclosed in the inventor's U.S. Pat. Nos. 7,824,185 and 7,726,841. The present invention differs from the arrangements disclosed in the inventor's prior patents in that the foldable light fixtures disclosed therein are limited to inclusion of outlet units or LED units, whereas the modified foldable light fixtures include light devices that can be changed to outlet devices on the different multiple surfaces so as to not only offer LED lighting but also outlets and other device with Internet, phone, motion sensor or other functions. It will be appreciated that the existing electric products to which multiple surface LED lights of the current invention's multiple surface LED light may be applied may be varied without departing from the scope of the current invention. In addition to the foldable devices, the light device of the preferred embodiments may be applied to the power strips, light fixture, and extension cord of the inventor's U.S. Pat. No. 7,824,185), the wall outlet device or LED light device of the inventor's U.S. Pat. No. 7,618,150, the foldable device or extendable device of the inventor's U.S. Pat. No. 7,722,230, the removable device of the inventor's U.S. Pat. No. 7,726, 839, and the transforming device of the inventor's U.S. Pat. No. 7,726,841. All these modified existing products will become very useful and practical items because of the addition of multiple functions to the original products, which should be make them more valuable for people.

Figures 10, 10A, 10B, 10C:
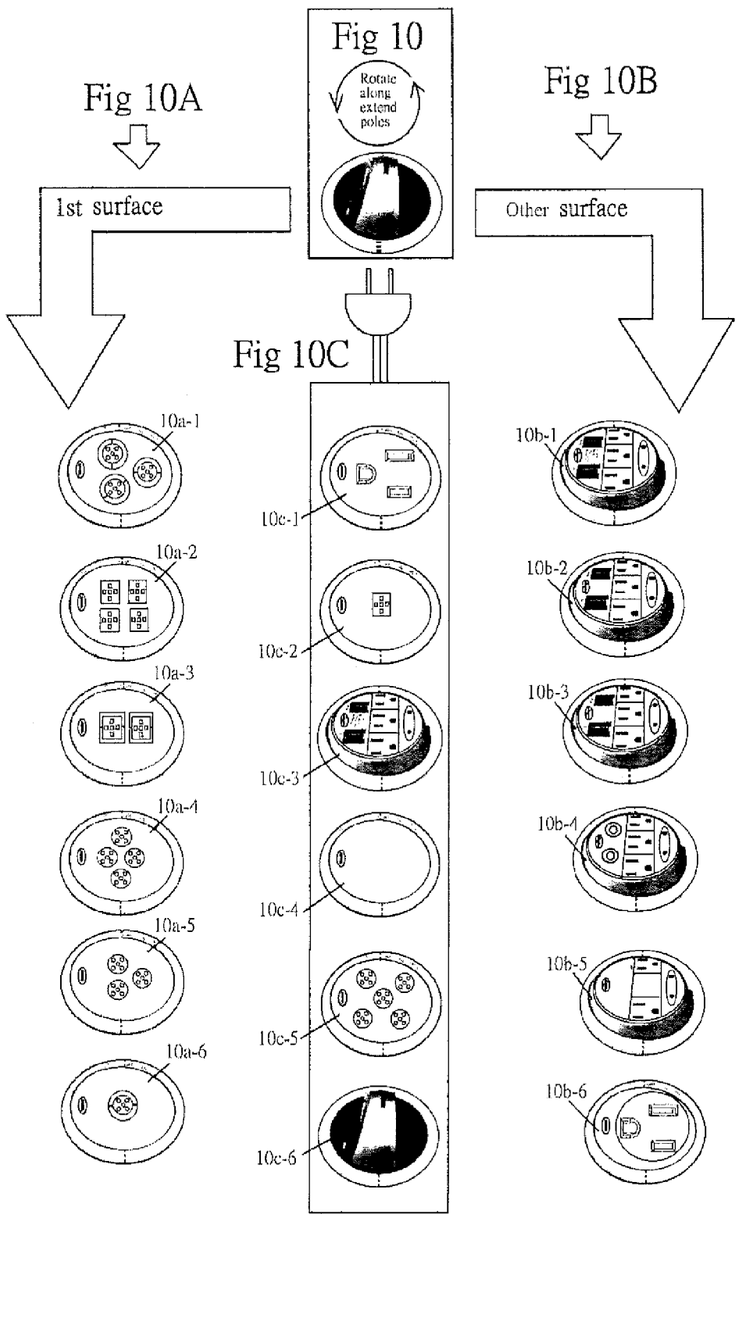

FIG. 10 shows other existing electric products to which the multiple surface light device of the present invention may be applied by adding multiple surface light devices to existing extension cords or power strips. Although the power strips have certain required specifications, it is possible to add an LED light to the outlet unit with only a limited change in dimensions because one can use an LED chip having a thickness of a few millimeters so that the multiple surface LED light with an outlet on another surface will have dimensions that are essentially the same as those of the outlet-units in the existing power strip despite the big increase in functions. For example, all power strips or extension cords can add the LED elements on a first surface and still keep the original outlet-units of the power strips or extension cords to enable the power strips or extension cords to become under-cabinet LED light units that allow people to change some of the LED lights into outlet-units other electric devices.

FIGS. 10, 10A, and 10B show different possible arrangements for the first surface (FIG. 10A) and the other surface as (FIG. 10B), with FIG. 10 show a power strip or extension cord that utilizes different first and second surface arrangements of the multiple surface LED lights.

Figure 11:
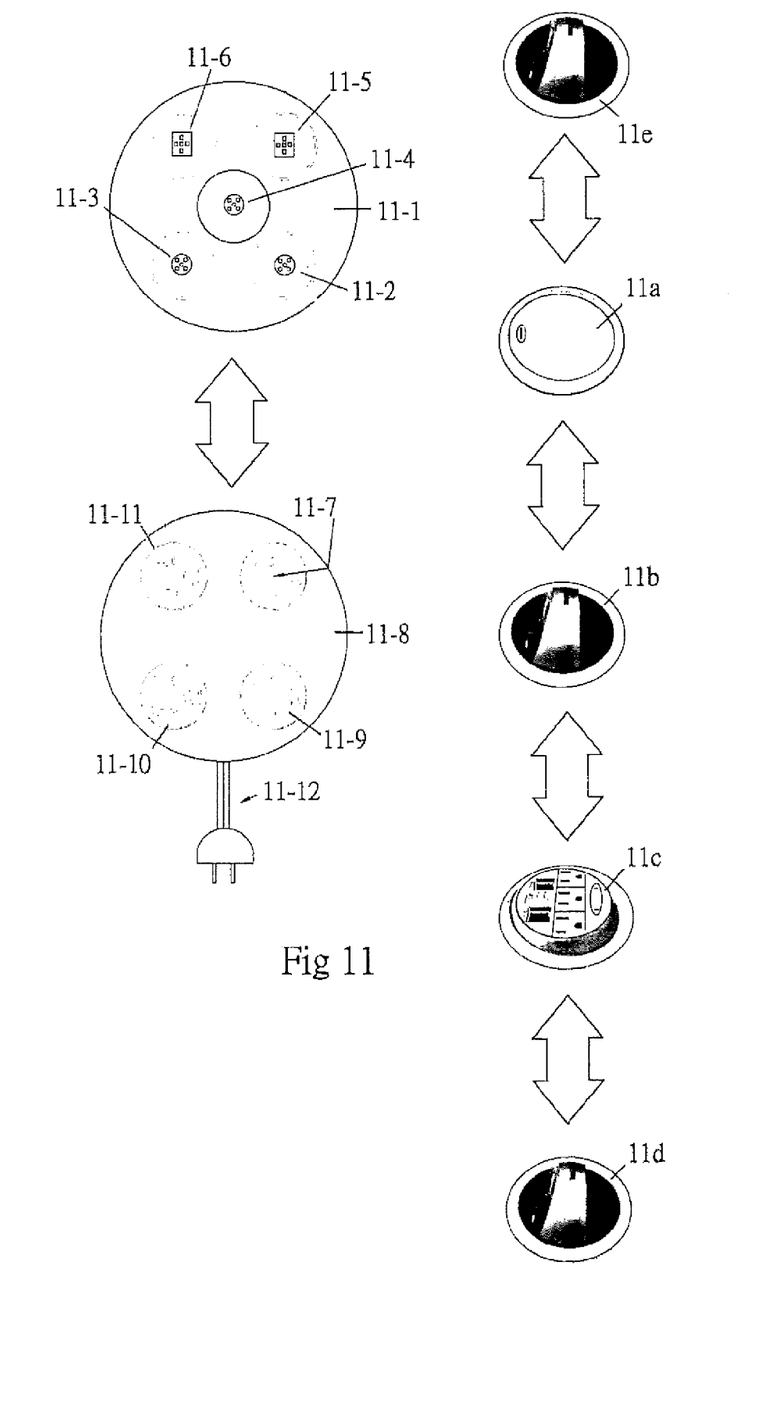

FIG. 11 shows another preferred embodiment in the form of a round power strip or extension cord which has a plurality of the multiple surface LED lights (11-2) (11-3) (11-5) (11-6) on its surface (11-1) and each of the LED lights (11-2) (11-3) (11-5) (11-6) has LED elements with a different style, thickness, shape, brightness, color, control means, circuit, turn-on/turn-off timing, sensor means, switch means, power output, and so forth. Each of these multiple surface LED lights can change surfaces, and in particular from surface (11-5) to surface (11-7), from surface (11-6) to surface (11-11), from surface (11-2) to surface (11-9), and from surface (11-3) to surface (11-10). The center unit (11-4) is not a multiple surface LED light. The side drawing shows how the multiple surfaces (11-2) (11-3) (11-5) (11-6) are changed by rotating from (11*a*) to (11-*b*) to (11-*c*) and to (11*d*), so that it is clear how to carry out a change from the first surface to another surface by external force, which may be manual or provided by a motor to automatically the design, or change the design by wireless remote control, or by other external force applying mechanisms depending on market requirements.

Finally, the manner in which electrical signal delivery is provided to the rotatable first and second surfaces may utilize the teachings of the inventor's prior U.S. Patent Publication No. 2008/0266856 and U.S. Pat. No. 7,824,185, the drawings of which are incorporated herein by reference and which show how to provide electric signal delivery from one end to another end of a rotatable, twisting, or movable coupling between units. Alternatively, the preferred embodiments may utilize any other conventional market-available skill to provide electric delivery from one movable part to another.

It is to be appreciated that the above description is not intended to be limiting, and that any alternative, same-function, or equivalent method or improvements may still fall within the scope of the current invention, i.e., that any LED light which has more than one surface and can change to other surfaces may fall within the scope of the current invention.

The invention claimed is:

1. A multiple surface LED light, comprising:
   a rotatable member having a first surface and at least one other surface, one of the first surface and the other surface being exposed to a user while the other surface is hidden from the user by a surface of another object or structure in which the rotatable member is rotatably mounted, wherein when the first surface is exposed and the other surface is hidden, rotation of the rotatable member upon application of an external force causes the other surface to be exposed and the first surface to be hidden,
   wherein the first surface includes at least one LED element arranged to emit light beams according to a predetermined function, output, color, effects, and performance;
   wherein the other surface includes at least one of the following devices: an electrical power outlet; adaptor; hub; USB socket; memory storage socket; memory stick socket; memory card socket; internet socket; interface card socket; additional light source; sound device; sensor device; alarm device, time related device; digital electrical device or processor; and digital data equipment; and
   means for rotatably mounting the rotatable member in a frame, support, or housing, the frame, support, or housing being fixed or held in a surface of said another object or structure selected from a desk, wall, ceiling, bar, tube, fence, closet, cabinet, power strip, extension cord, light fixture, light bar, door, window, rack, and electrical device for indoor or outdoor use,
   whereby rotation of the rotatable member with multiple surfaces enables the LED light to offer lighting and additional functions in the exposed area occupied by just one said surface.

2. A multiple surface LED light as claimed in claim 1, wherein a number of said at least one other surface is at least two said other surfaces.

3. A multiple surface LED light as claimed in claim 1, wherein said first surface has an arrangement of multiple LED elements.

4. A multiple surface LED light as claimed in claim 1, wherein the light device is mounted in a housing of a main object selected from a light fixture, light set, light device, and power strip to form a finished product.

5. A multiple surface LED light as claimed in claim 1, wherein the LED light incorporates means for supplying electrical signals to said at least one LED element to cause it to turn on and off to provide predetermined said effects and performance.

\* \* \* \* \*